United States Patent [19]

Sumikawa et al.

[11] 3,983,170

[45] Sept. 28, 1976

[54] PROCESS FOR THE PURIFICATION OF MALIC ACID

[75] Inventors: Shozo Sumikawa, Hofu; Rikichi Maida; Yuriaki Kageyama, both of Ube, all of Japan

[73] Assignees: International Organics, Inc., Duluth, Minn.; Kyowa Hakko Kogyo Co., Ltd., Tokyo, Japan; part interest to each

[22] Filed: Dec. 6, 1974

[21] Appl. No.: 530,194

[52] U.S. Cl. .......................... 260/535 P; 260/537 N
[51] Int. Cl.² .......................................... C07C 59/12
[58] Field of Search ..................................... 260/535

[56] References Cited
UNITED STATES PATENTS 3,371,112  2/1968  Winstron .......................... 260/535 P

*Primary Examiner*—Paul J. Killos
*Attorney, Agent, or Firm*—Glenn K. Robbins

[57] ABSTRACT

A process for the purification of D,L-malic acid. An aqueous solution of D,-L-malic acid containing maleic acid and fumaric acid as impurities is treated with a strongly basic anion-exchange resin to remove the maleic acid and fumaric acid to provide substantially pure D,L-malic acid.

5 Claims, 4 Drawing Figures

PROCESS FOR THE PURIFICATION OF MALIC ACID

SUMMARY OF THE INVENTION

This invention relates to a process for recovering purified D,L-malic acid from a aqueous solution of D,L-malic acid containing impurities. The impurities include maleic acid, fumaric acid, metal ions, organic coloring substances, etc. D,L-malic acid is utilized in great quantity as a food additive such as a seasoning or souring agent. Accordingly, it is most important to obtain high quality D,L-malic acid of less impurities.

With recent increase of a demand for D,L-malic acid, the output of D,L-malic acid synthesized industrially becomes greater than the output of D,L-malic acid obtained by purification of natural fruits. The synthesis of D,L-malic acid is generally accomplished by the method comprising heating an aqueous solution of maleic acid under pressure to hydrate maleic acid to D,L-malic acid. The reaction solution obtained by this reaction contains, in addition to the intended D,L-malic acid, such impurities as uncreated maleic acid, fumaric acid formed by the isomerization reaction, coloring substances considered to be formed by side reactions, and metal ions which are presumed to come from the reactor or the like. In general, the temperature of the reacted solution coming from the reactor is about 180°C. When this is cooled to a temperature approximating room temperature, the majority of fumaric acid which has a low solubility is precipitated in the form of crystals, which can be separated by filtration.

The so obtained filtrate (hereinafter referred to as "starting aqueous solution of D,L-malic acid") usually contains impurity acids, i.e., fumaric acid and maleic acid, in an amount of 3 to 5% based on the total acids.

As the method for separating purified D,L-malic acid from this starting aqueous solution of D,L-malic acid, there have heretofore been adopted such methods as a customary method for purification of organic substances comprising the steps of concentration, crystallization, separation and, if desired, recrystallization, and a method comprising adding calcium hydroxide to the starting aqueous solution to crystallize out D,L-malic acid in the form of calcium D,L-malate, recovering the crystal, separating the salt into D,L-malic acid and calcium and purifying so recovered D,L-malic acid. However, these conventional methods are very troublesome and obtained yields are very low. Further, in connection with the quality of the product, in the case of the former methods there is a problem that fumaric acid and maleic acid are readily incorporated, and the latter method includes a problem that the calcium component is readily incorporated.

We have made research with a view to developing a process which can overcome these defects of the conventional methods, and have arrived at the following interesting finding. More specifically, it has been found that when a mixed solution containing D,L-malic acid, fumaric acid and maleic acid is passed through a column packed with a strongly basic anion-exchange resin (for instance, Diaions SA 20A and SA 21A manufactured by Mitsubishi Chemical Industries LTD., Amberlites IRA-400 and IRA-410 manufactured by Rhom & Haas Co., etc.), the anion-exchange resin exhibits a highly selective adsorption to maleic acids, and an eluate containing only D,L-malic acid and fumaric acid and being substantially free of maleic acid is obtained.

As the strongly basic anion-exchange resin to be used in this invention, there may be mentioned, for instance, Diaions SA 10A, SA 101, SA 200, SA 20A, SA 201 and SA 21A manufactured by Mitsubishi Chemical Industries Ltd., Amberlites IRA-400, IRA-401, IRA-402, IRA-410 and IRA-411 manufacture by Rhom & Haas Co., Duolite A 101 manufactured by Chemical Process Co., Nalcite HCR-W manufactured by Dow Chemical Co. and Permutit S-2 manufactured by The Permutit Co. etc.

At first, we considered that in the case of a mixed aqueous solution of D,L-malic acid, fumaric acid and maleic acid, in order to separate maleic acid having a relatively great ionizing degree (primary dissociation constant $= 1.42 \times 10^{-2}$) from other acids having a relatively small ionizing degree (primary dissociation constant of D,L-malic acid $= 4.0 \times 10^{-4}$; primary dissociation constant of fumaric acid $= 9.50 \times 10^{-4}$) by selective adsorption, it would be possible to expel weak acids, i.e., D,L-malic acid and fumaric acid, by an action of maleic acid which is a strong acid, when a weakly basic anion-exchange resin is used, but when a strongly basic anion-exchange resin is employed, not only the strong acid but also the weak acids would undergo adsorption and because of the absence of the selective adsorption it would be impossible to expel D,L-malic acid and fumaric acid by an action of maleic acid. In view of the fact that a patent was granted to a process for purification of D,L-malic acid characterized by the use of a weakly basic anion-exchange resin (for instance, U.S. Pat. No. 3,371,112), the above consideration deems to be reasonable and universal one.

However, contrary to the above expectation, from experimental results obtained by us, it was confirmed that, as is specifically disclosed in Examples given hereinbelow, the use of a strongly basic anion-exchange resin gives a much better selective adsorption of maleic acid than the use of a weakly basic anion-exchange resin. Our opinion on this fact is that a weakly basic anion-exchange resin exhibits a low exchange rate to each of acids in the case of a mixed aqueous solution of acids having such a low ionizing degree as mentioned above and neither expelling of fumaric acids by maleic acid nor high selective adsorption of maleic acid connot be expected, whereas high selective adsorption of maleic acid, i.e., selectivity in the exchange adsorption caused by the difference in the ionizing degree, can be attained only when a strongly basic anion-exchange resin is employed.

OBJECTS OF THE INVENTION

The above features are objects of this invention. Further objects will appear in the detailed description below and will otherwise be apparent to those skilled in the art.

For purpose of illustration of this invention there are shown in the accompanying drawings examples thereof. It is to be understood that these drawings are only for purpose of example and that the invention is not limited thereto.

FIGURES

DESCRIPTION OF THE INVENTION

A mixed solution of D,L-malic acid and fumaric acid, from which the majority of maleic acid has been separated by the strongly basic anion-exchange resin, is passed through a column packed with active carbon (for instance, granular active carbon CAL manufactured by Pittsburgh Chemical Co.) to remove fumaric acid from the mixed solution. When the mixed solution of D,L-malic acid and fumaric acid is passed through such column packed with active carbon, high selective adsorption of fumaric acid is accomplished and it is possible to obtain an eluate containing D,L-malic acid alone and being substantially free of fumaric acid and maleic acid. Active carbon exhibits a relatively high adsorbing activity to unsaturated acids such as fumaric acid and maleic acid, and therefore, the purification of the starting aqueous solution of D,L-malic acid may be accomplished by employing only active carbon. However, a considerable amount of D,L-malic acid is simultaneously adsorbed by active carbon, resulting in reduction of the yield of D,L-malic acid. Therefore, it is desired to reduce the amount used of active carbon as much as possible. More specifically, when the starting aqueous solution of D,L-malic acid is once converted to a solution comprising merely D,L-malic acid and fumaric acid by removing maleic acid therefrom by a method not using active carbon and the resulting solution is treated with a small amount of active carbon to remove fumaric acid therefrom, effective removal of maleic acid and fumaric acid can be attained. As the method for selectively adsorbing and separating maleic acid in advance, a method using a strongly basic anion-exchange resin gives very excellent results.

The test results on which we have arrived at the above fact will now be illustrated in the following Examples 1 and 2.

EXAMPLE 1

Figure 1:
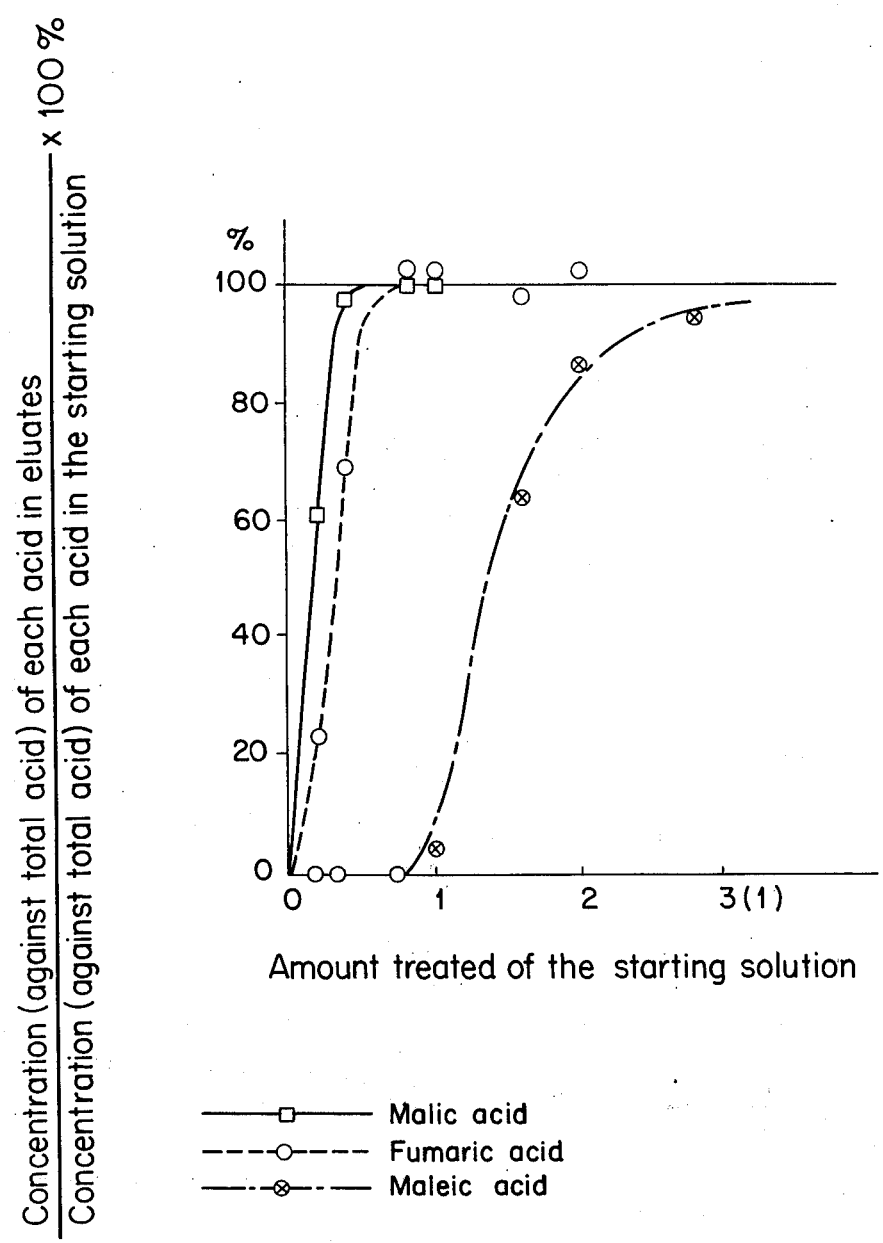
FIGS. 1 and 2 show curves illustrating changes of concentrations of each acid component in eluates obtained when mixed aqueous solutions of D,L-malic acid, fumaric acid and maleic acid are passed through columns packed with an ion-exchange resin.
Figure 2:
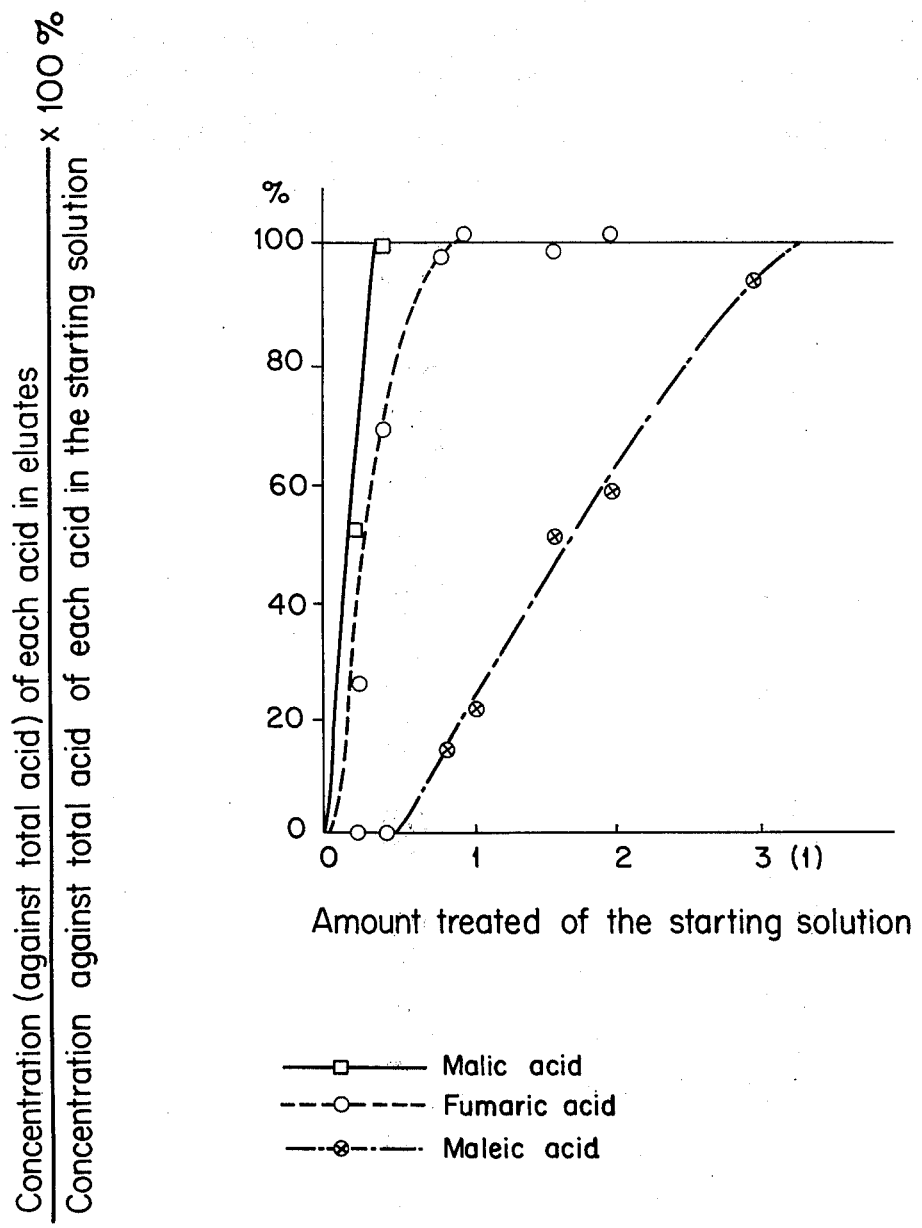

3 liters of a mixed aqueous solution containing 41.80% by weight of D,L-malic acid, 0.57% by weight of fumaric acid and 0.47% by weight of maleic acid was passed through a column having a diameter of 30mm and a length of 300mm, packed with 100ml of strongly basic anion-exchange resin, Diaion SA 20A manufactured by Mitsubishi Chemical Industries Ltd. (hereinafter abbreviated as "SA 20A"), and 3 liters of the same mixed aqueous solution was passed through a column having a diameter of 30mm and a length of 300mm, packed with 100ml of a waekly basic anion-exchange resin, Amberlite IR-45 manufactured by Rohm & Haas Co. (hereinafter abbreviated as "IR-45"). Changes of the concentrations of each acid in the eluates obtained in the above cases are shown in FIGS. 1 and 2, respectively. As is apparent from these Figures, when the mixed solution is passed through a column of SA 20A (FIG. 1), D,L-malic acid and fumaric acid are eluted out from the beginning, but the elution of maleic acid starts after 1 liter of the liquor has been passed through the column. In other words, in the case of this column of SA 20A, even if about 1 liter of the solution is passed through the column, it is possible to obtain a solution substantially free of maleic acid. On the other hand, in the case of the column of IR-45, (FIG. 2), although the tendency of the elution of D,L-malic acid and fumaric acid is almost the same as in the case of the column SA 20A, elution of maleic acid starts after about 0.5 liter of the solution has been passed through the column. Therefore, it is is intended to obtain an eluate substantially free of maleic acid by employing IR-45, it is necessary to stop the treatment while the amount treated of the starting solution is small.

EXAMPLE 2

Figure 3:
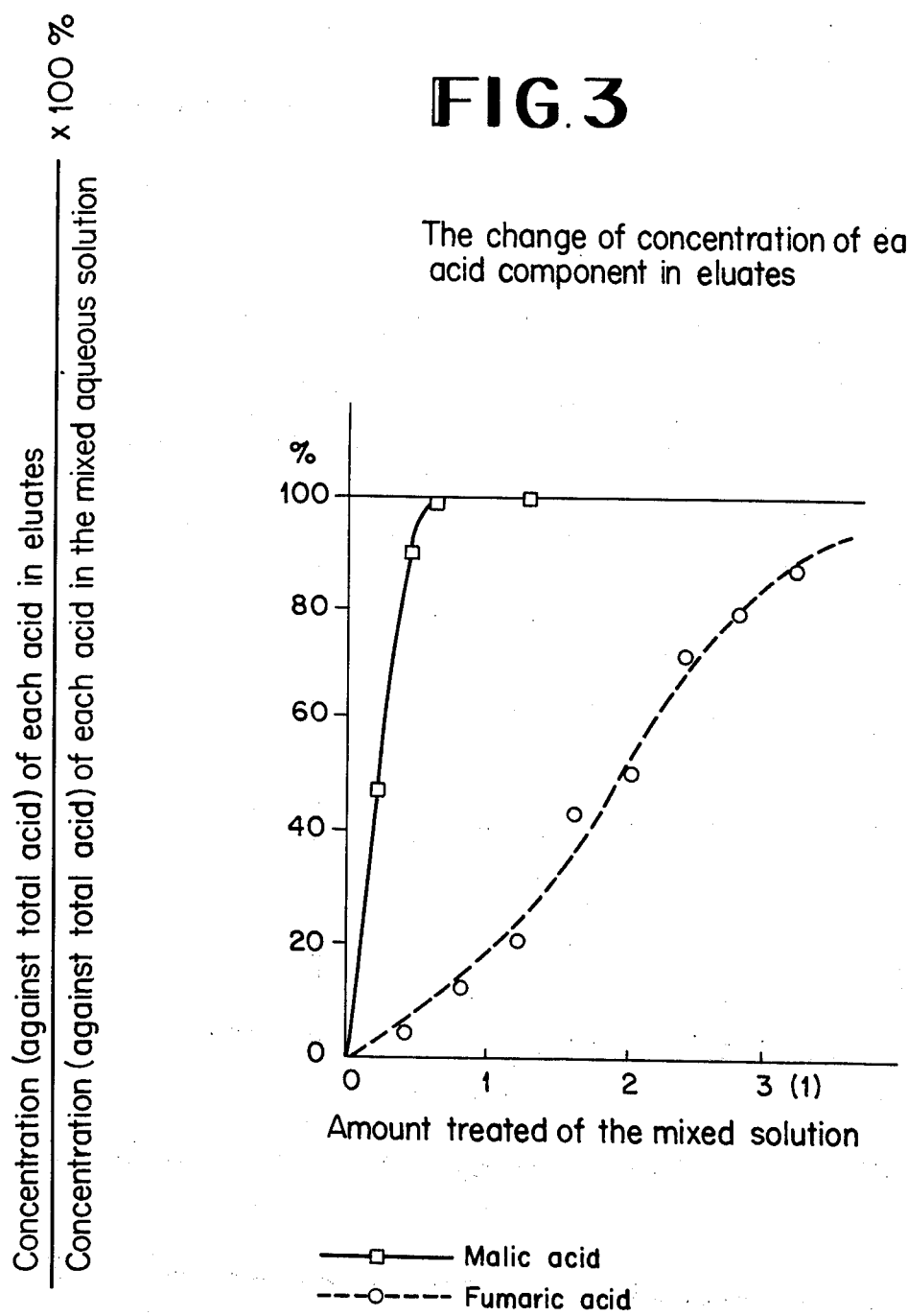
FIG. 3 shows a curve illustrating the change of concentrations of each acid component in an eluate obtained when a mixed aqueous solution of D,L-malic acid and fumaric acid is passed through a column packed with active carbon.

3 liters of a mixed aqueous solution containing 33.9% by weight of D,L-malic acid and 0.48% by weight of fumaric acid was passed through a column packed with CAL, granular active carbon manufactured by Pittsburgh Chemical Co. The change of the concentrations of the acids in the eluate is shown in FIG. 3. The elution curve of fumaric acid rises more slowly than that of D,L-malic acid.

Based on the above-explained fact, we have found that the following method is excellent for obtaining D,L-malic acid of a high purity from a starting aqueous solution of D,L-malic acid containing impurities with economical advantages. More specifically, the method comprises passing a starting aqueous solution of D,L-malic acid through a first column packed with a strongly basic anion-exchange resin to thereby remove maleic acid therefrom, passing the eluate through a second column packed with granular active carbon to thereby remove coloring substances, fumaric acid and, if present, a small quantity of maleic acid which has not been removed in the first column, and if desired, passing the eluate from the second column through a third column packed with a strongly acidic cation-exchange resin to thereby remove cations such as metal ions. The above treatments in the three columns may be conducted in succession. A small column packed with active carbon may be disposed before the first column to remove soloring substances in advance. As is illustrated in Example 1 given hereinbelow, crystals of D,L-malic acid of a high purity can be obtained from the resulting transparent aqueous solution of D,L-malic acid substantially free of impurities by conducting concentration and crystallization. On the other hand, when it is intended to obtain similar purifying effects by treating the starting aqueous solution under the same conditions as described above with respect to this invention while employing a combination of the first column packed with a weakly basic anion-exchange resin, and the second and third column packed, as described above, with granular active carbon and a strongly acidic cation-exchange resin, respectively, the necessary amounts of the anion-exchange resin and granular active carbon to be packed in columns increase extremely, as is apparent from comparison of results shown in Example 2 and Comperative Example give hereinbelow. Thus, this method is very inferior to the process of this invention from the economical viewpoint.

This invention will now be illustrated by reference to Example 1 and 2, and results of the case where a weakly basic anion-exchange resin was used instead of a strongly basic anion-exchange resin are illustrated in Comperative Example.

EXAMPLE 1

Figure 4:
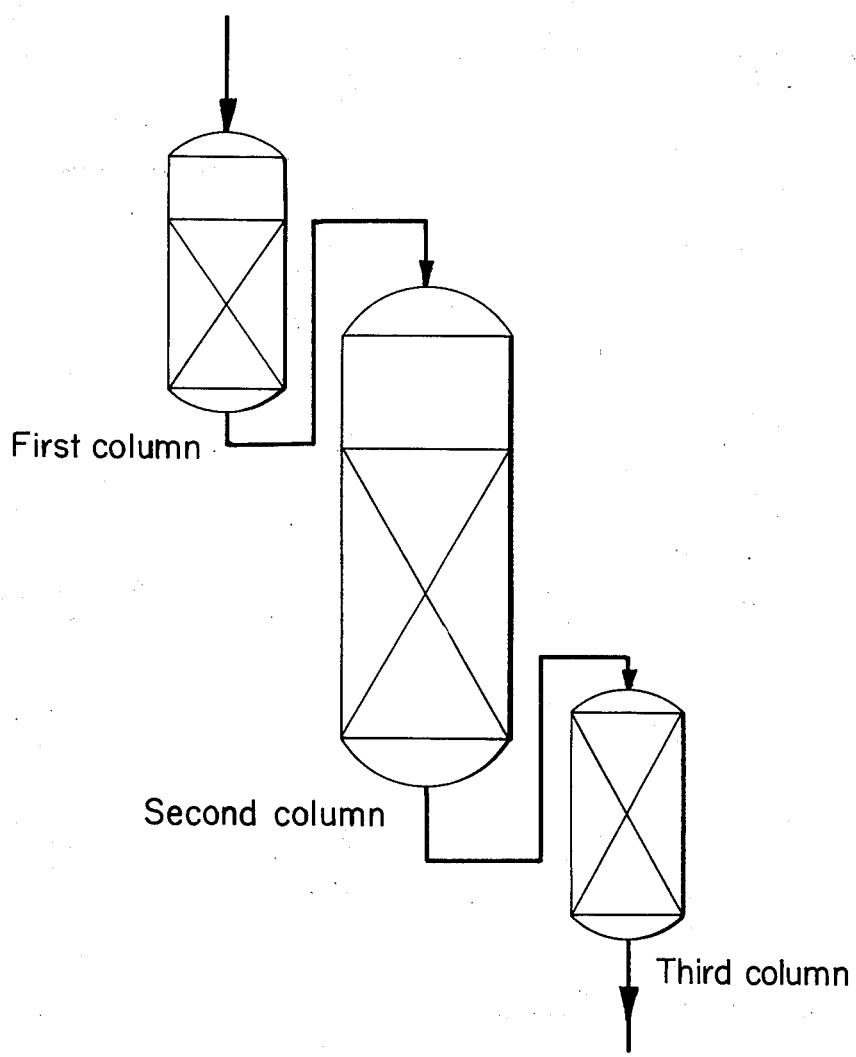
FIG. 4 is a diagram showing an embodiment of the arrangement of ion-exchange resin columns and granular active carbon columns for purification of a starting aqueous solution of D,L-malic acid.

Columns of ion-exchange resins and a column of active carbon were disposed as illustrated in FIG. 4, and fillers indicated in the following table were packed in the columns in amounts also indicated in the table.

| | Column Dimension (diameter × length) | Filler | Amount of Filler |
|---|---|---|---|
| First Column | 50 mm × 300 mm | strongly basic anion-exchange resin (Diaion SA 20A manufactured by Mitsubishi Chemical Industries Ltd.) | 450 ml |
| Second Column | 60 mm × 500 mm | granular active carbon (CAL manufacture by Pittsburgh Chemical Co.) | 700 ml |
| Third Column | 50 mm × 300 mm | strongly acidic cation-exchange resin (Diaion SKI manufactured by Mitsubishi Chemical Industries Ltd.) | 200 ml |

8.0 liters of a starting aqueous solution of D,L-malic acid was passed continuously through the first, second and third columns at a flow rate of 15 ml/min. The composition of the starting D,L-malic acid aqueous solution is as follows:

| D,L-malic acid | 37.30% by weight |
|---|---|
| Fumaric acid | 0.52% by weight |
| Maleic acid | 0.61% by weight |

At each time when 2.0 liters of the solution was eluted out, samples were collected at the outlets of the first and third columns and analyzed. Analysis values of the samples are shown in the table given below. The analysis values of the total eluate, whose volume was increased to 8.5 liters by incorporation of the washing liquor, are also shown in the line of "Total Eluate" of the table.

| | D,L-malic acid (% by weight) | Fumaric acid (% by weight) | Maleic acid (% by weight) |
|---|---|---|---|
| Samples Collected at Outlet of First Column | | | |
| at the time of elution of 2.0 liters | 35.9 | 0.48 | 0 |
| at the time of elution of 4.0 liters | 37.3 | 0.51 | 0 |
| at the time of elution of 6.0 liters | 37.3 | 0.59 | 0.15 |
| at the time of elution of 8.0 liters | 37.3 | 0.56 | 0.42 |
| Samples Collected at Outlet of Third Column | | | |
| at the time of elution of 2.0 liters | 32.0 | 0.01 | 0 |
| at the time of elution of 4.0 liters | 35.9 | 0.06 | 0 |
| at the time of elution of 6.0 liters | 36.9 | 0.19 | 0 |
| at the time of elution of 8.0 liters | 37.2 | 0.38 | 0 |

Total Eluate 8.5 liters of the so obtained eluate was concentrated to crystallize out 1.05kg of crystals of D,L-malic acid, whose analysis values are as follows:

| D,L-malic acid | 99.41 % by weight |
|---|---|
| Fumaric acid | 0.33 % by weight |
| Maleic acid | 0 % by weight |

EXAMPLE 2

Ion-exchange columns and an active carbon column were disposed as illustrated in FIG. 4, and fillers indicated in the following table were packed in these columns in amounts indicated in the table.

| | Column Dimension (diameter × length) | Filler | Amount of Filler |
|---|---|---|---|
| First Column | 60 mm × 600 mm | strongly basic anion-exchange resin (Amerlite IRA-410) | 900 ml |
| Second Column | 60 mm × 1000 mm | granular active carbon (CAL manufactured by Pittsburgh Chemical Co.) | 1400 ml |
| Third Column | 50 mm × 400 mm | strongly acidic cation-exchange resin (Diaion SKI manufactured by Mitsubishi Chemical | 400 ml |

-continued

| Column Dimension (diameter × length) | Filler | Amount of Filler |
|---|---|---|
| | Industries Ltd.) | |

20.80 kg of a starting aqueous solution of D,L-malic acid, having the following composition:

| D,L-malic acid | 41.40 % by weight |
|---|---|
| Fumaric acid | 0.76 % by weight |
| Maleic acid | 0.56 % by weight | was passed through the above columns to obtain, as a high concentration eluate suitable for concentration (rich-cut), 22.23 kg (19.3 liters) of an eluate having the following composition:

| D,L-malic acid | 36.13 % by weight |
|---|---|
| Fumaric acid | 0.14 % by weight |
| Maleic acid | 0.00 % by weight |

From the above results, the yield of D,L-malic acid from a starting aqueous solution of D,L-malic acid to a high concentration eluate obtained by passing the starting solution once through the columns was calculated to be 93.3 %.

COMPARATIVE EXAMPLE (Comparison to Example 2)

Fillers indicated in the following table were packed in columns used in Example 2 in amounts also indicated in the table.

| | Column Dimension (diameter × length) | Filler | Amount of Filler |
|---|---|---|---|
| First Column | 60 mm × 600 mm | weakly basic anion-exchange resin (Amberlite IR-45) | 1300 ml |
| Second Column | 60 mm × 1000 mm | granular active carbon (CAL manufactured by Pittsburgh Chemical Co.) | 1800 ml |
| Third Column | 50 mm × 400 mm | strongly acidic cation-exchange resin (Diaion SKI manufactured by Mitsubishi Chemical Industries Ltd.) | 400 ml |

20.80 kg of a starting aqueous solution of D,L-malic acid having the same composition as that of the starting solution used in Example 2 was passed through these columns to obtain, as a high concentration eluate suitable for concentration (rich-cut), 23.14 kg (20.2 liters) of an eluate having the following composition:

| D,L-malic acid | 34.47 % by weight |
|---|---|
| Fumaric acid | 0.17 % by weight |
| Maleic acid | 0.04 % by weight |

From the above result, the yield of D,L-malic acid from a starting solution of D,L-malic acid to a high concentration eluate obtained by passing the starting solution once through the columns was calculated to be 92.6 %.

What is claimed is:

1. A process for the purification of D,L-malic acid which comprises a step of passing an aqueous malic acid solution containing maleic acid, fumaric acid or a mixture thereof as impurities through a column of a strongly basic anion exchange resin.

2. The process of claim 1, wherein said malic acid solution is further treated with an active carbon.

3. The process of claim 2, wherein said active carbon is a granular active carbon having a size of 12 to 40 mesh.

4. The process of claim 1, wherein the malic acid solution is further treated with a strongly acidic cation exchange resin.

5. A process for purifying D,L-malic acid which comprises passing an aqueous malic acid solution containing maleic acid, fumaric acid or a mixture thereof as impurities through a column of a strongly basic anion exchange resin; and passing the eluate through a column of a granular active carbon and thereafter through a column of a strongly acidic cation exchange resin.

* * * * *